United States Patent [19]

Atkov et al.

[11] Patent Number: 4,483,344
[45] Date of Patent: Nov. 20, 1984

[54] DEVICE FOR POSITIONING CARDIOGRAPHIC SENSOR

[76] Inventors: Oleg J. Atkov, Petrovskaya alleya, 18, kv. 13, Moscow; Anatoly V. Popov, ulitsa Mira, 11, kv. 23, Mytischi Moskovskoi oblasti; Nurmukhamed M. Mukharlyamov, ulitsa Bronnaya, 29, kv. 73, Moscow; Vladimir F. Baranov, prospekt Koroleva, 2, kv. 23, Kaliningrad; Jury N. Belenkov, ulitsa Volgina, 9, korpus 1, kv. 84, Moscow; Alexandr N. Frolov, ulitsa Vokzalnaya, 14, kv. 39; Nikolai G. Odintsov, prospekt Koroleva, 8, kv. 48, both of Kaliningrad; Galina A. Fomina, Pribrezhny proezd, 1, korpus 1, kv. 64, Moscow, all of U.S.S.R.

[21] Appl. No.: 473,262

[22] Filed: Mar. 14, 1983

Related U.S. Application Data

[63] Continuation of Ser. No. 221,283, Dec. 30, 1980, abandoned.

[51] Int. Cl.$^3$ .............................................. A61G 10/00
[52] U.S. Cl. ................................ 128/661; 128/303 B; 128/644
[58] Field of Search ................ 128/24 A, 639, 644, 128/660–663, 670, 671, 701, 715, 303 B; 248/660–663

[56] References Cited

U.S. PATENT DOCUMENTS

| | | | |
|---|---|---|---|
| 2,582,776 | 1/1952 | Greenberg et al. | 250/490 |
| 2,625,074 | 1/1953 | Nistri | 248/662 |
| 2,927,575 | 3/1960 | Sherman | 128/24 A |
| 2,968,302 | 1/1961 | Fry et al. | 128/24 A |
| 3,338,235 | 8/1967 | Gordon | 128/24 A |
| 3,476,104 | 11/1969 | Davis | 128/639 |
| 3,624,744 | 11/1971 | Munger | 128/661 |
| 3,744,479 | 7/1973 | Stein et al. | 128/661 |
| 3,893,449 | 7/1975 | Lee et al. | 128/24 A |
| 4,002,915 | 1/1977 | Weiss et al. | 250/320 |
| 4,137,777 | 2/1979 | Haverl et al. | 128/660 |
| 4,151,834 | 5/1979 | Sato et al. | 128/661 |
| 4,154,230 | 5/1979 | Lee | 128/661 |
| 4,270,547 | 6/1981 | Steffen et al. | 128/671 |
| 4,293,771 | 10/1981 | Lescrenier | 250/491 |
| 4,308,870 | 1/1982 | Arkans | 128/671 |
| 4,341,220 | 7/1982 | Perry | 128/303 B |

FOREIGN PATENT DOCUMENTS

| | | | |
|---|---|---|---|
| 2735722 | 2/1979 | Fed. Rep. of Germany | 128/661 |
| 1281533 | 7/1972 | United Kingdom | 128/715 |
| 202452 | 4/1968 | U.S.S.R. | 128/303 B |

OTHER PUBLICATIONS

Nilsson, "A Combined Microphone for Simultaneous Recording of Pulse and Heart Sounds", Biomedical Engineering vol. 8, No. 10, Oct. 1973.

Primary Examiner—Edward M. Coven
Assistant Examiner—Max F. Hindenburg
Attorney, Agent, or Firm—Fleit, Jacobson, Cohn & Price

[57] ABSTRACT

Described herein is a device for positioning and fixing an echosignal sensor and sensors of electric signals in an apparatus for taking cardiograms having an echocardiograph and an electrocardiograph. The device has a base with two mutually perpendicular guideways for the movable carriage to travel thereon. The carriage carries a swivel head with a socket for accommodating the echosignal sensor. The swivel head is angularly displaceable in such a way that the centers of rotation of the socket and of the head itself coincide. The sensors of electric signals are fixed stationary on the base.

8 Claims, 4 Drawing Figures

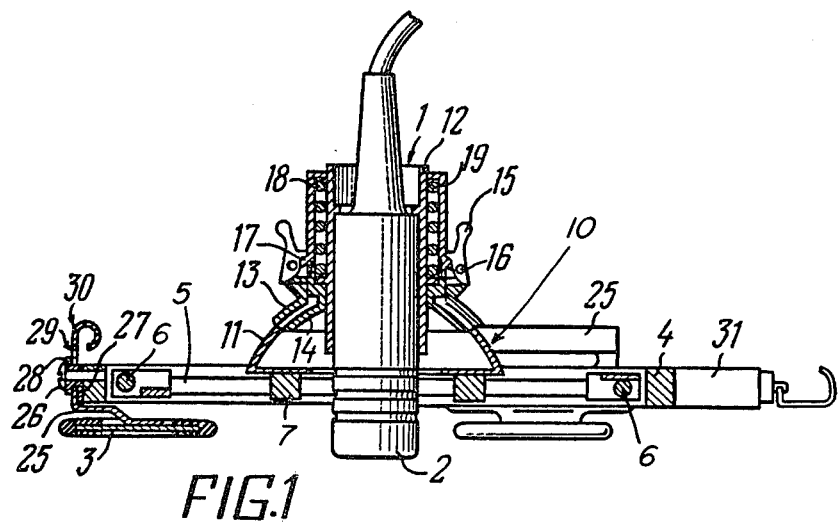
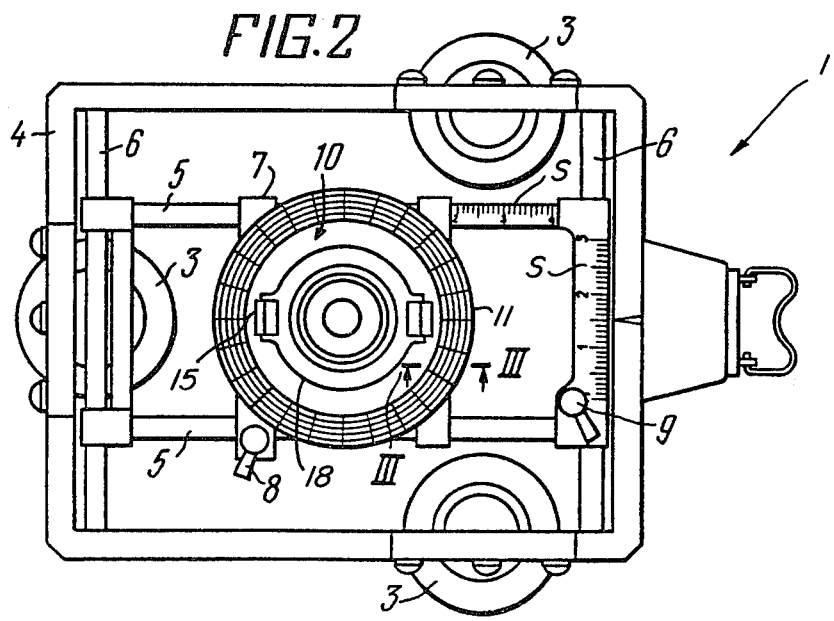

DEVICE FOR POSITIONING CARDIOGRAPHIC SENSOR

This application is a continuation, of application Ser. No. 221,283, filed Dec. 30, 1980 now abandoned.

FIELD OF THE INVENTION

The present invention relates to medicine and is concerned more specifically with apparatus for taking cardiograms, comprising an echocardiograph and an electrocardiograph and adapted for simultaneously taking an electrocardiogram and an echocardiogram.

BACKGROUND OF THE INVENTION

It is common knowledge that most reliable findings are obtained when taking an echocardiogram and an electrocardiogram at the same time and that accurate and reliable fixing of the echosignal sensor with respect to the point involved in the examination process is decisive for accuracy and reliability of the examination findings. However, the cardiologist with previously known devices has to move the echosignal sensor, press it against the patient's body and keep it in position with the help of his hand alone, which of course fails to provide adequately high accuracy of positioning and fixing the echosignal sensor, especially in view of the fact that the cardiologist's hand is liable to become fatigued in the course of examination performed. Furthermore, such a way of fixing the sensor fails to provide examination when the patient being examined is to perform some physical exercises. Ultimately, inasmuch as each of the electrocardiographic sensors is fixed individually, the examination time is much extended.

OBJECTS OF THE INVENTION

It is an object of the present invention to provide an accurate positioning and fixing of the echosignal sensor of an echocardiogram taking apparatus comprising an echocardiograph.

Another object of the present invention is to provide higher accuracy of examination findings when taking echo- and electrocardiograms.

One more object of the present invention is to cut down the examination time.

Finally, among other objects we shall note providing a possibility of taking precision-accuracy measurements with the patient performing various physical exercises.

SUMMARY OF THE INVENTION

The aforesaid and other objects of the present invention are accomplished due to the fact that provision is made in an apparatus for taking cardiograms, comprising an echocardiograph and an electrocardiograph, for a device for positioning and fixing the sensors of echosignals and electric signals connected to the echo- and electrocardiographs. The device incorporates a base with means for its arranging and fixing on the patient's body within the zone under examination, a movable carriage, two mutually perpendicular guideways for mounting and for guiding movement of the movable carriage. Retainers are provided on the carriage to lock it in a required position on the guideways. A swivel head is angularly adjustable on said carriage and has a socket for accommodating the echosignal sensor. The head is so made that when it is swivelled to an angle the center of rotation of the socket coincides with the center of rotation of the head itself and both centers are permanently situated at the same common point, said base having at least three sockets for accommodating the sensors of electric signals.

Advantageous features of the device discussed above reside first and foremost in the provision of precision accuracy of positioning and fixing the echocardiograph and ECG sensors attainable due to a possibility of accurate two-coordinate traversing of the carriage carrying said echosignal sensor, as well as precision-accuracy angular displacement of said echosignal sensor and its fixing at a preset point.

On the other hand, high-accuracy examination findings are attained due to a rigid coordinate linkage between the sensors at the instance of taking electrocardiograms. It is also worth noting that the proposed device is capable of high-precision measurements when the patient under examination performs various physical exercises. It is likewise obvious that the sensor positioning time is much reduced, whereby a total examination time is cut down as well, since all sensors are mounted on a common base.

According to one of the embodiments of the present invention the swivel head incorporates a hemispherical case with flat bases to be mounted on the carriage and with a hole in the central portion for a sleeve serving to accommodate the echosignal sensor, as well as two part spherical members carrying said sleeve and embracing the latter, one from outside and the other from inside. The part spherical members are mounted with a possibility of being brought together or apart so that when brought apart said members can be swivelled along with the sleeve to an angle with respect to a preset point, while when brought together said members and the socket are fixed rigidly in position. Such a constructional arrangement of the swivel head enables the echosignal sensor to be moved accurately with respect to a preset point within solid angle and to fix said sensor reliably through the entire examination process.

In order to provide reliable pressing of the echosignal sensor against the patient's body it is expedient to make use of a cup-mounted spring with one of its ends acting against the cup end and with the other, against the sleeve.

To provide convenient replacement of the echosignal sensor the swivel head may be made detachable.

BRIEF DESCRIPTION OF THE DRAWINGS

In what follows the present invention will be illustrated in a detailed description of specific embodiments of a device for positioning and fixing echosignal and ECG sensors adapted for use in an apparatus for taking cardiograms provided with an echocardiograph and an electrocardiograph to be read in conjunction with and with reference to the accompanying drawings, wherein:

FIG. 1 is a sectional view of one embodiment of a device for realization of the present invention;

FIG. 2 is a plan view of FIG. 1;

DESCRIPTION OF THE PREFERRED EMBODIMENTS

Figure 3:
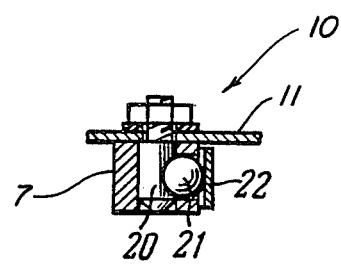
FIG. 3 is a view along line III—III of FIG. 2, on an enlarged scale.

Referring now to FIGS. 1 and 2 one can see that in apparatus, according to the present invention, for simultaneously taking echo- and electrocardiograms, provision is made for a device 1 adapted for positioning and fixing an echosignal sensor 2 and sensors 3 of electric signals, said sensors 2 and 3 being connected to an echocardiograph and an electrocardiograph (not shown in the drawings).

The device 1 comprises a base 4 which mounts mutually perpendicular guideways 5 and 6, the guideways 6 being stationary, while the guideways 5 are traversable along the guideways 6, whereby a carriage 7 can travel in two mutually perpendicular directions. Graduated scales "S" are carried by parts of the guideways 5 and 6. Retainers 8 and 9 are provided for locking the carriage 7 in place. The carriage 7 carries a swivel head 10 incorporating a hemispherical case 11 graduated on its outside surface, said case 11 having a flat base mounted on the carriage and a hole in the central portion thereof for passage of a sleeve 12, said sleeve serving as a socket for accommodating the echosignal sensor 2. Two part spherical members 13 and 14 embrace the case 11 from outside and inside, respectively, and carry the sleeve 12. The members 13 and 14 are mounted with a possibility of being brought together and apart so that when brought apart said members can be swivelled along with the sleeve 12 with respect to a preset point in a plane perpendicular to the plane of the carriage. The center of rotation of the sleeve 12 coincides with the center of rotation of the head itself, and both centers are permanently situated at the same common point. When said members are brought together, the sleeve and the members 13 and 14 are rigidly fixed in place due to the fact that shaped cams 15 loosely set on pivots 16 are turned till meeting stops 17. An axial spring 19 is mounted in a cup 18 screwed onto the member 14 outside of the sleeve 12, said spring positioned with one of its ends against the end of the cup 18, and with the other, against the sleeve 12, thus exerting a constant force pressing the echosignal sensor 2 to the patient's body.

Figure 4:
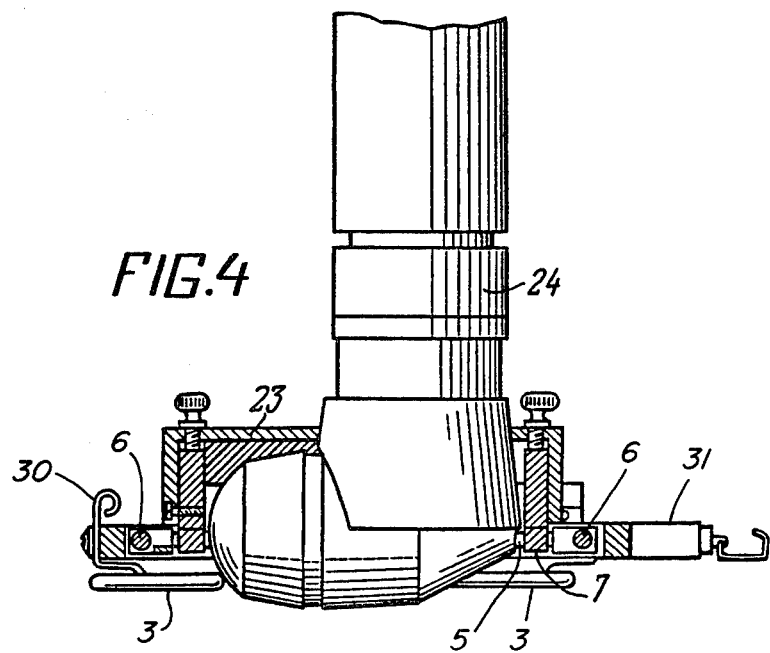
FIG. 4 is a view of a swivel head with a multibeam sensor used with a modification of the device of FIG. 1.

The swivel head 10 is made detachable and is mounted on the carriage 7 by inserting rods 20 (FIG. 3) into holes provided in the carriage 7 until balls 21 retained within the holes and biassed by a spring 22 catch the respective recesses in the rods 20. After removal of swivel head 10, a swivel head 23 with a multibeam sensor 24 (FIG. 4) is set in position in a similar way. The sensors 3 are fixed in position on the base 4 through metallic holders 25 (FIG. 1) made fast on the base 4 by screws 26, said holders serving both as current leadouts of the sensors 3 and as means for connecting these to the electrocardiograph. The holders 25 are made from a current-conducting metal and have a special shape making possible their use as a support for fastening on the patient's body; they are electrically insulated from the base through gaskets 27 and bushes 28. The sensors 3 themselves are secured on the holder projection under the base so as to be pressed to the patient's body. The other portion of the holder, projecting upwards with respect to the base 4, has a slot 29 for passage of the belt when fastening the device on the patient's body and a contact socket 30. The contact sockets 30 of all the sensors are connected to a common socket 31, which is adapted to be connected to the electrocardiograph.

The device of the present invention operates as follows.

The echosignal sensor 2 is fitted into the sleeve 12 and oriented vertically, the members 13 and 14 are brought together by turning the cams 15 till they meet the stops 17, and the device is made fast on the patient's body within the area to be examined, using belts (not shown) passed through the slots 29. Then the wire leads of the electrocardiograph are connected to the socket 31 through an appropriate cable, whereupon the swivel head 10 is lightly forced upwards from the carriage 7 and removed, after which a lubricant is applied to the patient's body within the square area over which the echosignal sensor will be moved. Next the swivel head is mounted onto the carriage by bringing the head rods 20 in register with the holes in the carriage, which is attained by lightly pressing the head until a characteristic click is heard.

Thereupon the members 13 and 14 are brought apart by moving the cams 15 down, and the cardiologist, while holding the cup 18, searches for a required examination point by moving the carriage 7 along the guideways 5 and 6, at the same time observing the echosignal sensor readings from the monitor. Then the carriage is fixed at the thus-selected point using the retainers 8, 9, and examination is carried out by displacing the members 13, 14 with respect to the hemispherical case 11, said members being connected, through the cup 16 and the sleeve 12 to the echosignal sensor 2, so that the members 13 and 14 describe a solid angle round the point in question. As soon as the desired zone of examination is located, the members 13, 14 are brought together by turning the cams 15 till they meet the stops 17, and further examination procedure is carried out without touching the echosignal sensor.

In order to replace the swivel head carrying a single-beam echosignal sensor with the swivel head 23 carrying the multibeam echosignal sensor 24, one must force the former head out of the carriage and bring the rods 21 out of the holes in the carriage, then take out said head and mount the head 23 instead.

While a specific and preferred embodiment of the present invention has been disclosed hereinbefore, it will be understood that various modifications and versions may occur to those skilled in the art without departing from the spirit and scope of the invention.

Thus, for instance, the shaped cams may be substituted by spring actuated buttons with rollers. However, in any case the above-discussed embodiment of the present invention is by no means limitative on the scope of the invention as defined by the claims that follow.

What we claim is:

1. In an apparatus for taking cardiograms having an echocardiograph and an electrocardiograph, a device for positioning and for fixing the position of an echosignal sensor and the positions of sensors of electric signals, said echosignal and electric signal sensors being connected, respectively, to said echocardiograph and said electrocardiograph, said device comprising:

a base, means for fixing the base on the patient's body within the zone under examination, a movable carriage, two mutually perpendicular guideways carried by said base for mounting and for guiding movement of the movable carriage, retainers for locking the carriage in a required position in the guideways, a swivel head rotatable with respect to said carriage about a common point to be examined and having a sleeve for accommodating the echosignal sensor and for holding said echosignal sensor in contact with the patient's body, said swivel head being rotatable to place said echosignal sensor in one of several monitoring positions while said carriage is locked in the required position in said guideways, said swivel head and sleeve being rotatable about the common point, wherein the swivel head incorporates a hemispherical case with a flat base mounted on the carriage and defining a through opening in a central portion thereof for said sleeve and the swivel head further including two partly spherical members carrying said sleeve and embracing the hemispherical case, one from outside and the other from inside;

means for mounting said members to allow said members to be moved together and apart so that when said members are moved apart, said members can be swivelled along with the sleeve to an angle with respect to the common point to be examined, and when said members are moved together, said members and the sleeve are fixed rigidly in position; and at least three sockets connected to and electrically insulated from said base, said sockets adapted for accommodating said sensors of electric signals.

2. A device as claimed in claim 1, wherein the swivel head and at least one of the guideways are provided with graduated portions.

3. A device as claimed in claim 1, wherein a cup-mounted axial spring is provided outside of the sleeve, said spring positioned with one of its ends against the cup end, and with the other, against the sleeve so as to press the sleeve along with the sensor towards the patient's body.

4. A device as claimed in claim 1, wherein the swivel head is made detachable from said carriage.

5. A device as claimed in claim 1, wherein the swivel head carries a multibeam sensor.

6. A device for positioning an echosignal sensor and sensors of electric signals on a patient's body, said device comprising:

a base positionable on the body of a patient so that the patient's body supports the device;

first and second guide means, said first guide means being fixed to said base and supporting said second guide means for movement;

a carriage slidably mounted on said second guide means, said carriage being movable in a first direction by movement of said second guide means along said first guide means and being movable in a second direction by movement of said carriage with respect to said second guide means;

first retainer means for fixing the position of said second guide means with respect to said first guide means;

second retainer means for fixing the position of said carriage with respect to said second guide means, said first and said second retainer means fixing the position of said carriage with respect to the base;

an echosignal sensor carried by said carriage;

a swivel head, said swivel head including a sleeve angularly displaceable with respect to said carriage for supporting said echosignal sensor and for holding said echosignal sensor in contact with the patient's body, said sleeve allowing said echosignal sensor to be positioned in one of several monitoring positions while the position of said carriage is fixed with respect to said base wherein the swivel head incorporates a hemispherical case with a flat base mounted on the carriage and said hemispherical case defining a through opening in a central portion thereof for said sleeve and the swivel head further including two partly spherical members carrying said sleeve with one partly spherical member contacting the hemispherical case from the outside and the other partly spherical member contacting the hemispherical case from the inside;

means for mounting said members to allow said members to be moved together and apart so that when said members are moved apart, said members can be swivelled along with the sleeve to an angle with respect to the common point to be examined, and when said members are moved together, said members and the sleeve are fixedly rigidly in position; and a plurality of sensors of electric signals carried by and electrically insulated from said base and positionable in contact with the patient's body.

7. A device according to claim 6, wherein said base has at least one opening formed therein for passage of a belt used to hold the base in a desired position on the body of a patient.

8. A device according to claim 6, wherein a swivel head is removably connected to said carriage, said swivel head having a portion thereof rotatable with respect to said carriage and having a socket formed therein receiving the echosignal sensor.

* * * * *